US005471606A

United States Patent [19]
Huang et al.

[11] Patent Number: 5,471,606
[45] Date of Patent: Nov. 28, 1995

[54] INFORMATION STORAGE AND PROCESSING

[75] Inventors: Han Huang, Agoura Hills; Craig A. Morioka, Los Angeles; Osman Ratib, Pacific Palisades; Paul N. S. Cho, Culver City; Bruce K. T. Ho, Los Angeles, all of Calif.; Takeo Sonobe; Toru Shinagawa, both of Toride, Japan

[73] Assignees: The Regents of the University of California, Oakland, Calif.; Hitachi Maxwell, Ltd., Ibaraki, Japan

[21] Appl. No.: 212,066

[22] Filed: Mar. 14, 1994

Related U.S. Application Data

[62] Division of Ser. No. 967,558, Oct. 27, 1992, Pat. No. 541,676, which is a continuation of Ser. No. 401,146, Aug. 31, 1989, abandoned.

[51] Int. Cl.⁶ .......................... G11B 7/007; G06F 13/00
[52] U.S. Cl. .................... 395/500; 364/DIG. 2; 364/952.31; 364/952.6; 364/963.5; 369/44.26; 369/275.1
[58] Field of Search ...................... 395/425, 600, 395/500; 382/64, 65; 369/44.26, 275.1, 273

[56] References Cited

U.S. PATENT DOCUMENTS

| | | |
|---|---|---|
| 3,886,325 | 5/1975 | Dorr et al. . |
| 4,141,005 | 2/1979 | Bonner et al. . |
| 4,281,315 | 7/1981 | Bauer et al. . |
| 4,419,750 | 12/1983 | Howe . |
| 4,433,377 | 2/1984 | Eustis et al. . |
| 4,485,439 | 11/1984 | Rothstein . |
| 4,559,614 | 12/1985 | Peck et al. . |
| 4,661,988 | 4/1987 | Shimizu . |
| 4,682,305 | 7/1987 | Ishikawa ................................ 395/425 |
| 4,760,526 | 7/1988 | Takeda et al. . |
| 4,791,558 | 12/1988 | Chatin et al. . |
| 4,802,152 | 1/1989 | Markvoort et al. . |
| 4,827,462 | 5/1989 | Flannigan et al. ........................ 369/32 |
| 4,833,471 | 5/1989 | Tokuume et al. . |
| 4,866,601 | 9/1989 | Dulac et al. . |
| 4,896,289 | 1/1990 | Svinicki et al. . |
| 4,918,661 | 4/1990 | Yamguchi . |
| 4,956,806 | 9/1990 | Crowe et al. . |
| 5,034,914 | 7/1991 | Osterlund ................................ 395/425 |
| 5,040,232 | 8/1991 | Kanno ....................................... 382/44 |
| 5,053,945 | 10/1991 | Whisler ..................................... 395/600 |
| 5,070,474 | 12/1991 | Tuma et al. . |

FOREIGN PATENT DOCUMENTS

| | | |
|---|---|---|
| 20165382 | 12/1985 | European Pat. Off. . |
| 20372703 | 6/1990 | European Pat. Off. . |
| 3823252A1 | 1/1989 | Germany . |

OTHER PUBLICATIONS

Mankovich et al., *RSNA Annual Meeting*–UCLA (1986), "Operational Radiologic Image Archive on Digital Optical Disks".

Huang et al., *Medical Imaging Technology* 4:2 (1986) "PACS at UCLA I—A Status Report".

R. H. van Bilderbeek et al. *IBM Technical Disclosure Bulletin*, 12(2):683, Jul. 1972, "Device–Independent Conversion Program".

*Primary Examiner*—Krisna Lim
*Attorney, Agent, or Firm*—Merchant, Gould, Smith, Edell, Welter & Schmidt

[57] ABSTRACT

Data and directories are separated and stored on separate parts of an optical disk. Directories are on the inner tracks and data are on the outer tracks, in a first format. Data and directories are written from magnetic disk storage in a different second specific format that is determined by a particular operating system used by an information processor. A medical information processing system is provided with an external magnetic disk storage and the optical disk.

35 Claims, 11 Drawing Sheets

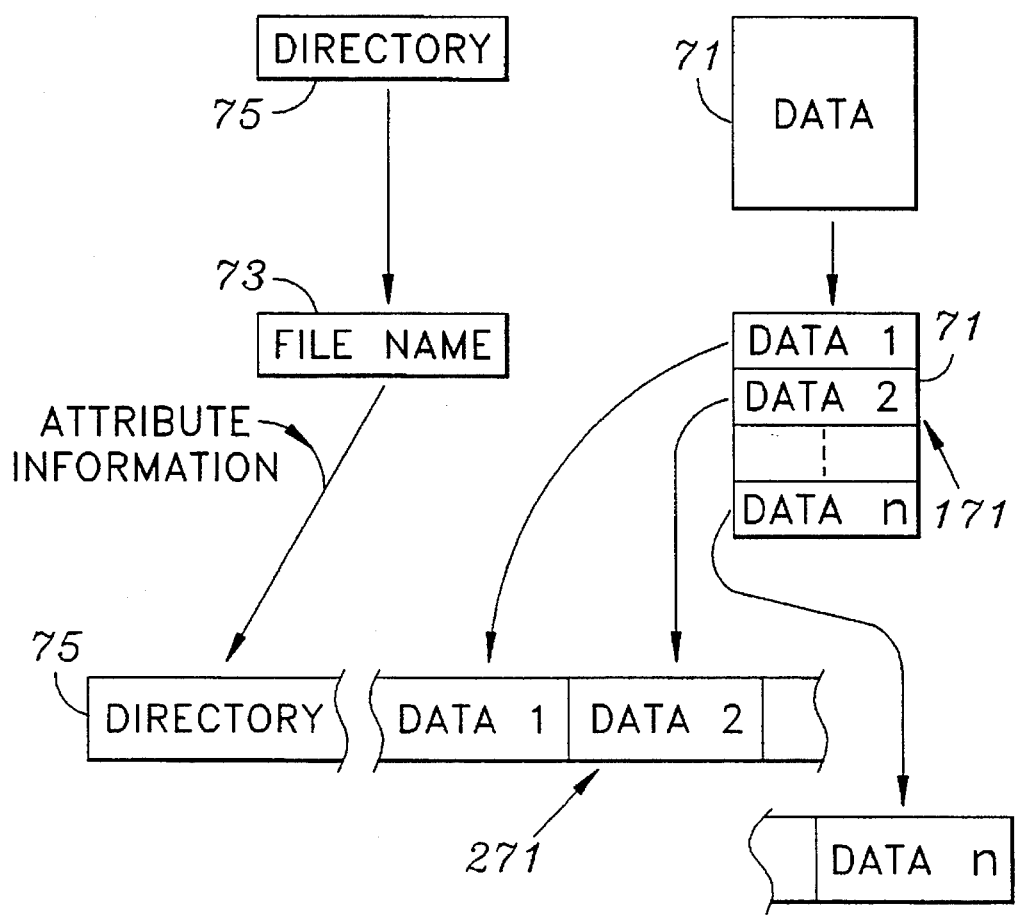
FIG. 8  FORMAT CONVERSION OF DATA RETRIEVED FROM MAGNETIC DISK

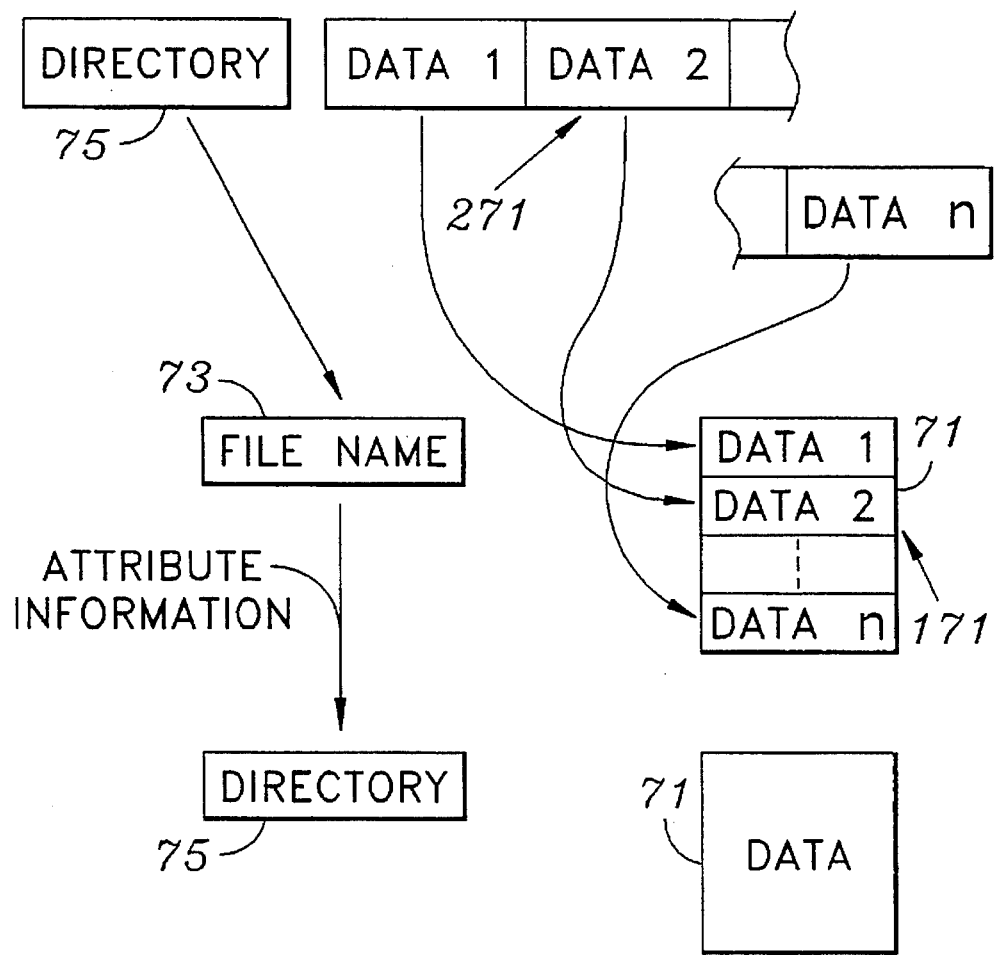
FIG. 9 FORMAT CONVERSION OF DATA RETRIEVED FROM OPTICAL DISK

INFORMATION STORAGE AND PROCESSING

This is a division of the application Ser. No. 07/967,558, filed on Oct. 27, 1992, now the U.S. Pat. No. 5,410,676, which is a continuation of the application Ser. No. 07/401,146, filed Aug. 31, 1989, now abandoned.

BACKGROUND

This invention relates to an information processing system. More particularly the invention is directed to an information storage and processing system that is effectively configured to ensure compatibility of removable stored media among different systems.

Apparatus of this type includes optical disk filing systems and word processors which store information in different proprietary formats. These different formats are inconvenient and have hindered the spread of such systems, because removable stored media from one system are not compatible with other systems. Accordingly, information stored on one system has not been usable on another system.

More particularly the invention concerns 5.25-inch and 3.5-inch optical disks which conform to ISO SC23. The storage capacity of a 3.5-inch optical disk is about 100 megabytes (MB), and that of a 5.25-inch optical disk is about 600 MB. The storage capacity of such discs is much greater than the capacity of equivalent physical size other storage media such as magnetic disks.

Recently there have been studies for using such media to store personal medical history data. In a radiological application, a single conventional x-ray with a resolution of 2,048 by 2,048 pixels by 10 bits requires 5 MB of storage space. An ultrasound sonogram requires about 0.25 MB, and a nuclear magnetic resonance (NMR) image requires about 0.07 MB.

Due to the enormity of the radiological data needed to be stored, it has been a developing practice at least in one hospital, namely, the UCLA Medical School in Los Angeles, Calif., to store this data on mainframe optical discs. These are physically about 12" to 14" discs and are permanently housed in mainframe computer storage facilities as part of a digitally based picture archiving and communicating system (PACS). This system replaces conventional x-ray films operating systems. A problem with PACS, however, is the difficulty of data retrieval. PACS is structured on a "first-in-first stored" system, and hence when particular data is required about a particular patient, a long lead time is necessary to assemble all that data for display.

By recording a patient's diagnostic data on an optical disk file, it is possible to maintain an up-to-date record of each patient's entire medical history. This would be useful for diagnostic purposes. To date this has not been possible with existing storage media.

Computer systems have made progress in recent years, and a variety of systems are now available. For instance, personal computers commonly used in hospitals and physician offices are currently based essentially on either an IBM PC/AT (Trademark), Macintosh (Trademark), or SUN (Trademark) information processing systems. The term IBM PC/AT processing system includes diferent clone systems. Such operating systems however are basically incompatible and this limits the ability to process information and transfer data from one system to another.

It is desirable in carrying out a diagnosis, that stored personal medical information be usable on different computer systems within the same hospital or at other hospitals. It should also be possible to record and store data obtained in the radiologic diagnosis on the storage media operable with the different computer systems.

With conventional information processing systems, storage media and computer systems this has not yet been achieved.

SUMMARY

An object of the invention is to provide an information processing system which is highly usable. The system seeks to solve the incompatibility problems between different conventional computer, processing and storage systems.

Another object of the invention is to provide a compatible system that can be used with optical disks containing data stored in a compatible format that differs from the storage format used by the operating system of a computer system concerned. It is an object to provide a system which employs essentially a digital or binary format for data processing, storage and display which is essentially compatible with multiple computer operating systems.

Compatibility between different systems can be achieved by making the information stored on removable media the same, or partly the same, and providing each system with a translation capability.

According to the invention an information processing system comprises an information processor for processing information, the processor having a specific operating system. There is an external storage for connection to the information processor, the external storage having data and directories written and read in a first format based on the specific operating system.

A format converter for connection to the external storage and the information processor converts data and directories in the first format from the external storage to data and directories in a second format. The format converter includes designation means for designating different areas for storing the data and the directories in the second format. The format converter also converts data and directories from the second format to the first format.

An optical disk drive connected to the format converter permits storing of the data and the directories in the second format on an optical disk.

The designation means includes sequential storage means whereby the directories are recorded sequentially on the optical disk starting from an inner track and the data are recorded sequentially on the optical disk starting from an outer track. There is means for dividing data read from the external storage into an optical disk sector portion.

Also respective designation means designates that the data and the directories read from the optical disk by the optical disk drive are each stored in a continuous form in one area of the external storage. Different format data and directories separately read from the optical disk by the optical disk drive are combined and converted to data in the first format.

Further according to the invention, there is a method for processing and storing data in an information processing system provided with an information processor, a magnetic disk system for connection to the information processor and for storing data designated by the information processor, and an optical disk drive for storing data designated by the information processor. Data and directories in a first format based on a specific operating system of the information processor are combined, and the combined data and directories are stored on the magnetic disk system.

The data and directories stored on the magnetic disk system are separated in the first format, and the data in the first format is divided into sector units used by the optical disk in the optical disk drive. The divided data is stored on the optical disk and directories containing file names are stored onto the optical disk on which data divided into sector units have been stored.

In data storing, the data are written sequentially onto the optical disk in sector length units, starting from an outer track. In directory storing, the directories are written sequentially starting from an inner track.

With the invention, medical information can be stored on a removable and portable optical disk. This disk can then be inputted into different computer systems, which would otherwise have normally have incompatible operating systems. The information can then be read out into the different computer systems for information processing. Moreover, new information and data can be written onto the disk by the different computer operating systems.

The invention is further described with reference to the accompanying drawings and an embodiment using optical disks as a removable storage media.

DRAWINGS

FIGS. 8, 8a and 9 illustrate the format conversion of data being transferred between an optical disk and a magnetic disk of the external storage;

DESCRIPTION

Figure 1:
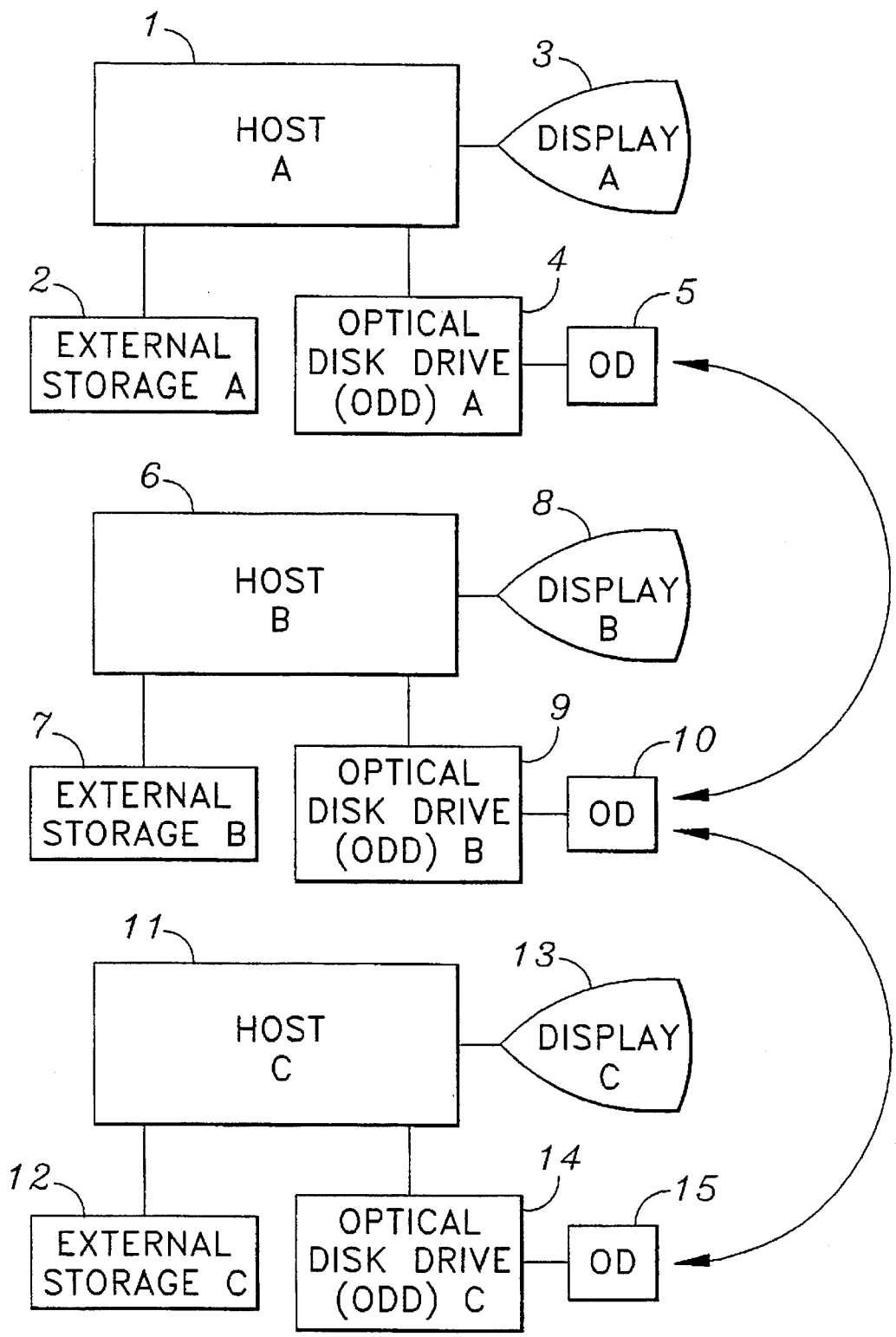
FIG. 1 illustrates a computer system configuration of an embodiment of three different computer systems showing the intercompatibility through the optical disks.

With reference to FIG. 1, a system configuration comprises a host computer system 1. The computer usually is at least a 16-bit model. There is also a first storage, namely, an external storage 2 such as a magnetic disk, and a display 3 capable of a resolution of at least 1,024 by 1,024 pixels by 8 bits. An optical disk drive 4 for 5.25-inch or 3.5-inch disks is connected with the computer system 1. An optical disk 5, namely, a second storage, which has stored data is supplied for the disk drive 4.

In FIG. 1, the system configuration is illustrated for a computer system A, designated by numeral 1, computer system B designated by numeral 6, and computer system C designated by numeral 11. Each of these computer systems, A, B and C, could respectively be different. For instance, an IBM PC/AT (Trademark) Macintosh (Trademark) or SUN (Trademark) system. The operating systems are respectively different. As indicated, each has its own optical disks 5, 10 and 15 respectively. The arrowed line interconnecting the three optical disks 5, 10, 15 designations indicates that the disks 5, 10 and 15 is intercompatible with any of the systems.

Figure 2:
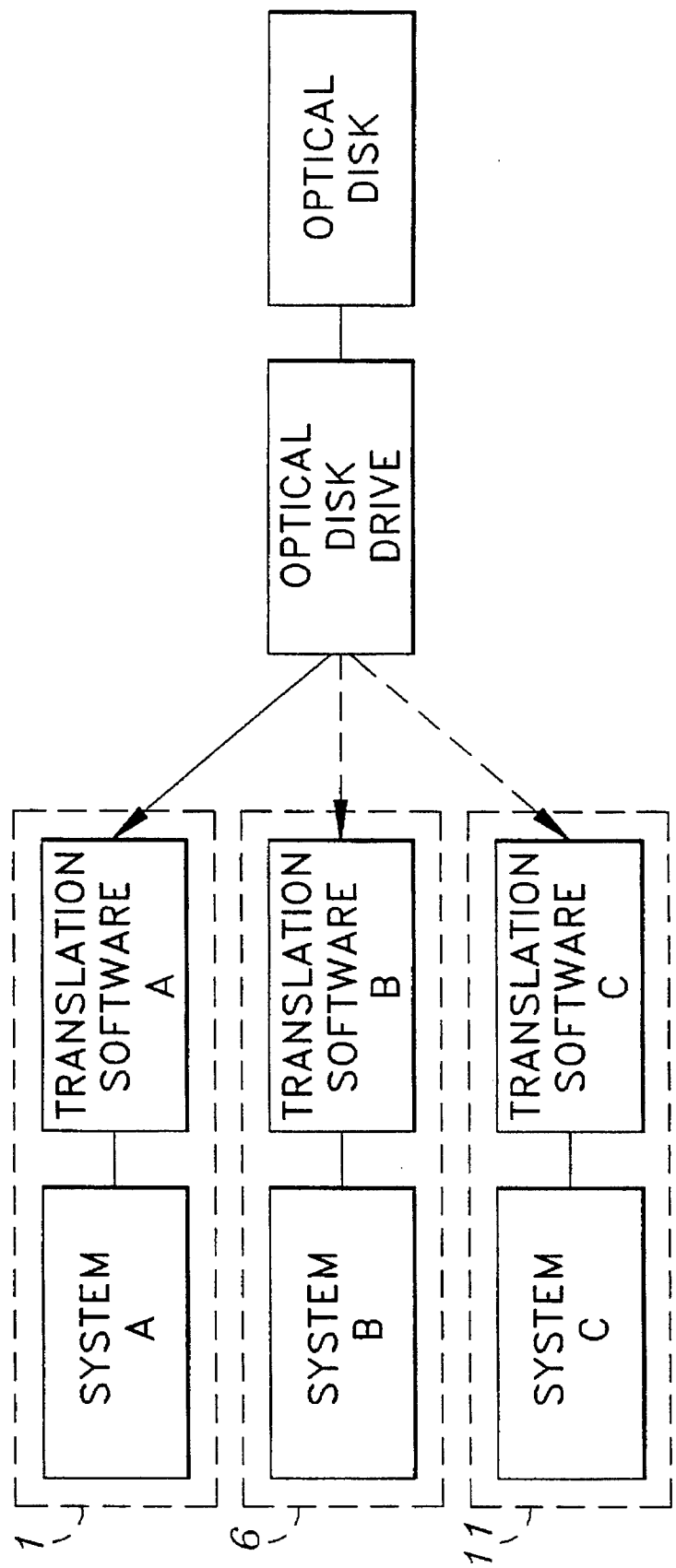
FIG. 2 illustrates an embodiment of the filing format and operation of three different computer systems.

FIG. 2 illustrates a specific optical disk filing format and computer system operation. This format is the same on all computer systems A, B and C. An optical disk drive is used to perform optical disk read/write operations when connected to one or another of the computer systems A, B or C. Since each system A, B and C handles files in a different way, additional translation software A, B or C respectively is required to convert the files for each respective computer system, A, B or C. Thus three different translation software programs A, B and C would be provided to render the optical disk information accessible to the respective computer systems 1, 6 and 11. This permits for the optical disk data to be read, processed and stored in the external storage 2, 7 and 12, respectively, of each computer system 1, 6 and 11, and the optical disk drives 4, 9 and 14 of those systems. Specifically, the data can be displayed on respective screens 3, 8 and 13 of the respective computer systems. This is further illustrated in FIG. 3.

Figure 3:
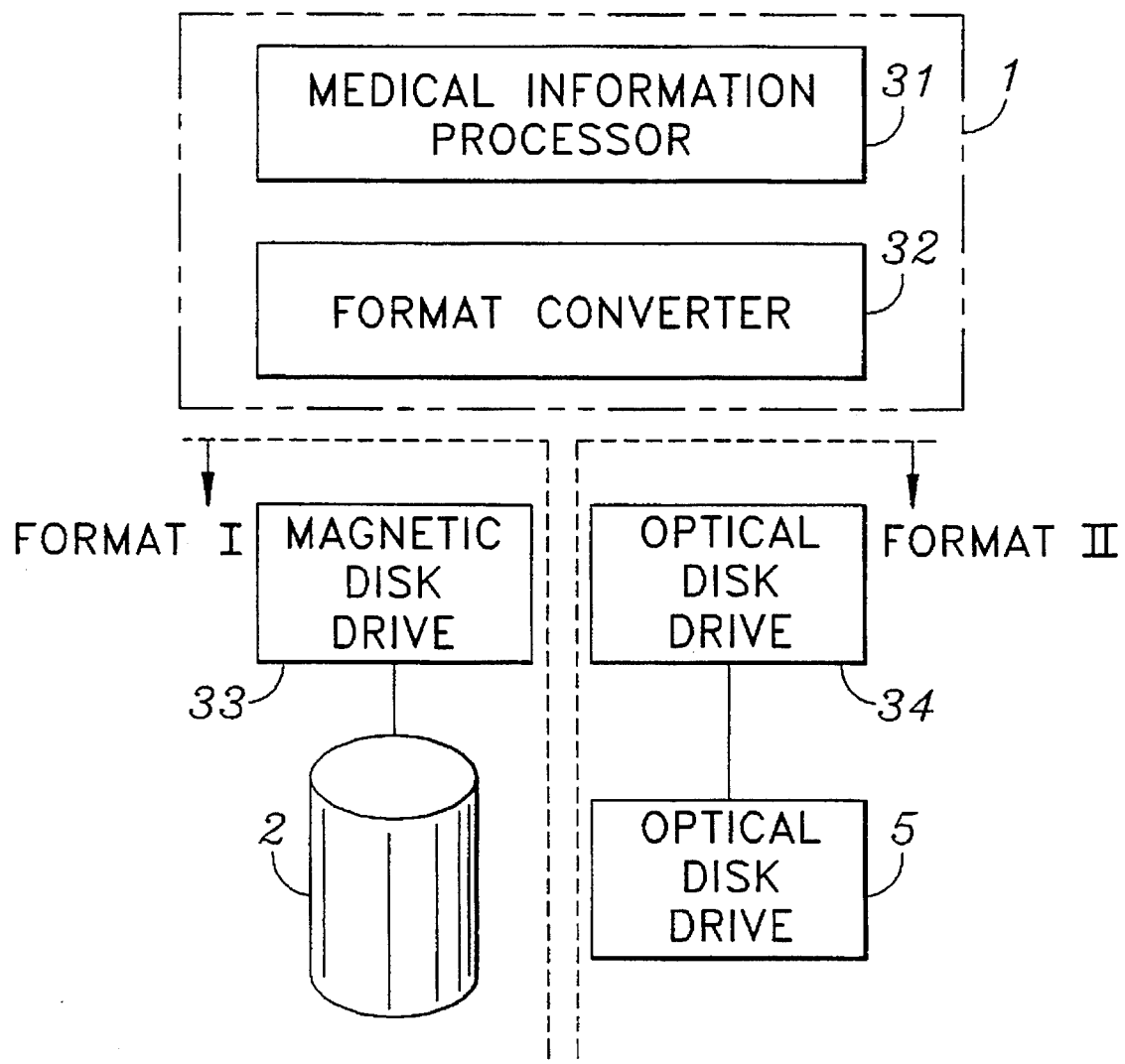
FIG. 3 is an explanatory drawing showing an embodiment of the software configuration of an exemplary computer system.

FIG. 3 shows an example of the software configuration of a medical information processing system. A medical information processor section 31 converts and outputs data read in from the optical disk 5 or data input from an external source 2. Programs and data for the computer system 1 are usually stored in the external floppy magnetic disk storage 2 in the first format used by the operating system concerned. This format is termed Format I. A magnetic disk drive 33 is equipped with the ability to write to the external storage 2 data converted to Format I by a format converter 32, and to read out data from the external storage 2.

Each computer system 1 is equipped with a format converter 32 for data conversion between a first format in which the data is stored on a magnetic disk external storage 2 and to a second format for stored on the optical disk 5. An optical disk drive 34 is provided with the capabilities of reading and writing data. Medical image and other such data are stored on the optical disk 5 in a second format. This format is termed Format II. When the data stored on the optical disk 5 are to be read out, displayed or otherwise processed by the medical information processing section 31, data that have been read out in Format II are converted by the format converter 32. The converted data is sent to the medical information processing section 31 from the format converter 32.

Data conversion between the external storage 2 and the optical disk 5 is also possible. In this case the format converter 32 converts each such Format I or II to the other Format II or I respectively. Thus, when using a format I that differs from Format II of the operating system data stored on the external storage 2 and the optical disk 5 can be made uniform by conversion between Formats I and II without depending on the operating system. Compatibility is thus provided among the plurality of different computer systems 1, 6 and 11.

Figure 4:
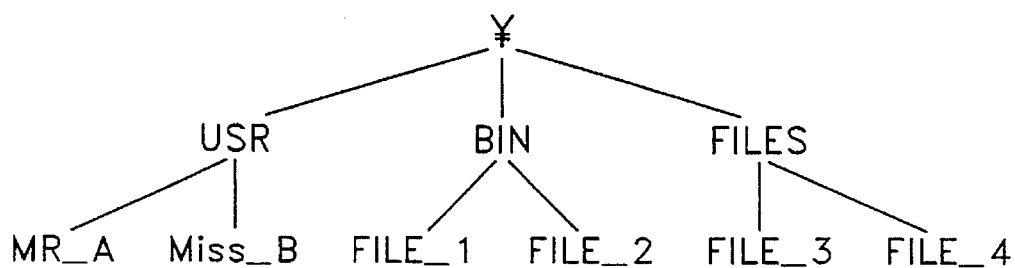
FIGS. 4 and 5 illustrate the directory structure of the external storage for an exemplary computer system.
Figure 5:
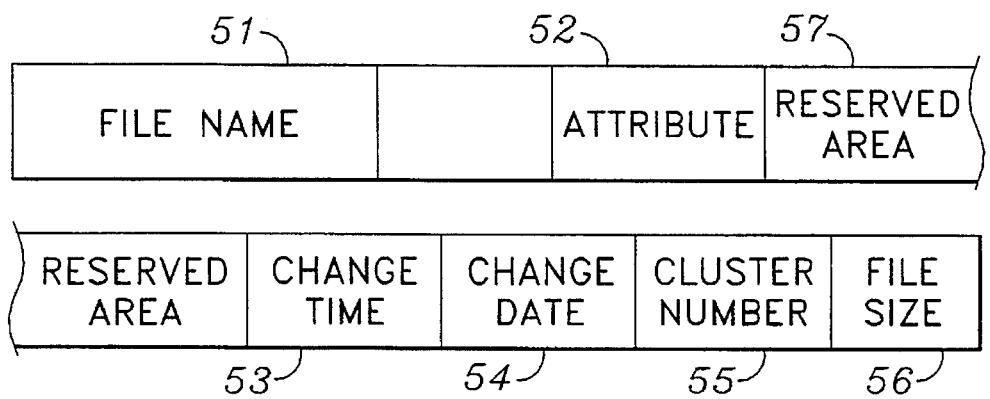

Image data in files are stored on an external storage 2 for the computer system 1 host computer A in a Format I based on the particular used operating system used. FIGS. 4 and 5 illustrate the directory structure of an external storage 2, showing the location and type of the image data.

As indicated in FIG. 4, and for the purposes of the description, it is assumed that the image data is in FILE 3. Image file FILE 3 can be accessed on the basis of the directory information. In FIG. 5 the directory information is illustrated. This includes a file name 51 given to each file, attribute 52 indicating the type of file, and the time 53 and date 54 the file was recorded on the disk 5. The header cluster number indicates the first data set of the file, and the file size 56.

Figure 6:
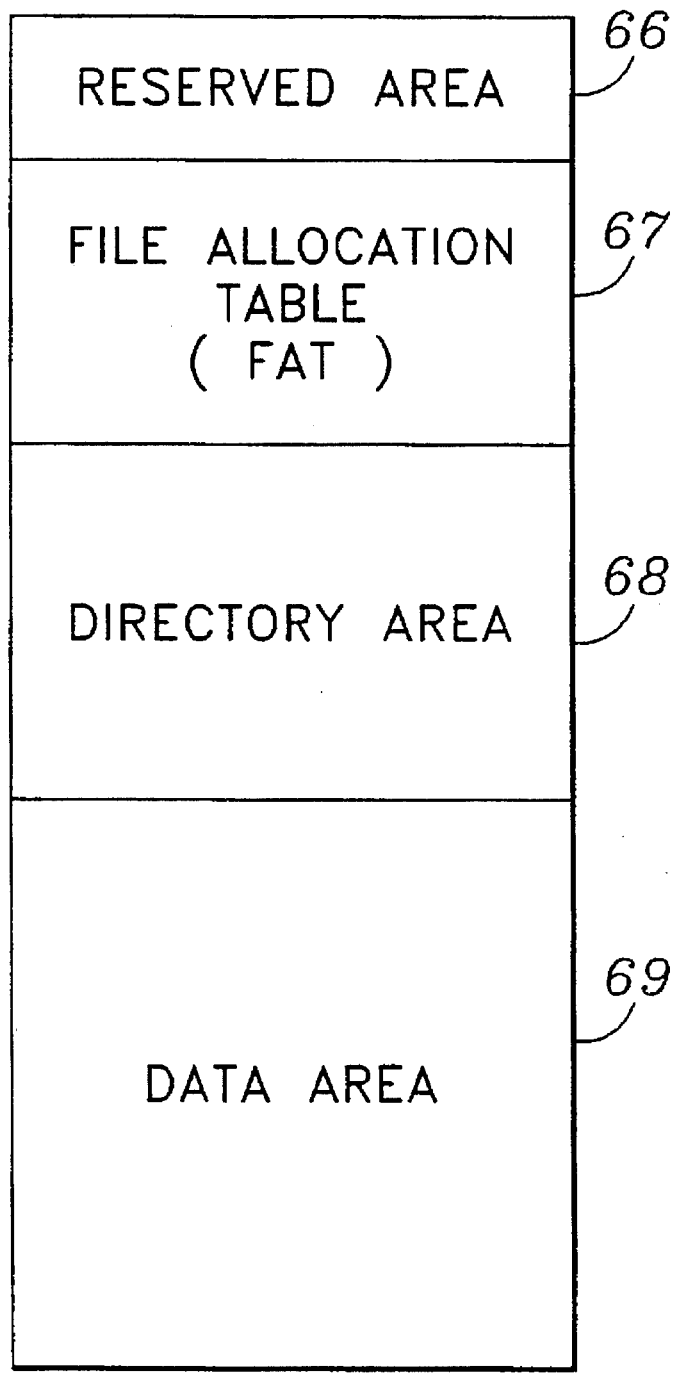
FIG. 6 shows the memory map of the external storage.

The external storage 2 contains four areas shown in the memory map of FIG. 6. There is a reserved area 66, a file allocation table (FAT) area 67, a directory area 68 and a data area 69. The data area 69 is divided into sectors, which form the access units and clusters. Each of these consists of a plurality of sectors. External access is performed on a cluster basis. The FAT area 67 has locations corresponding to each of the clusters in the data area. This includes the number of the cluster containing the next portion of the data in the file.

Figure 7:
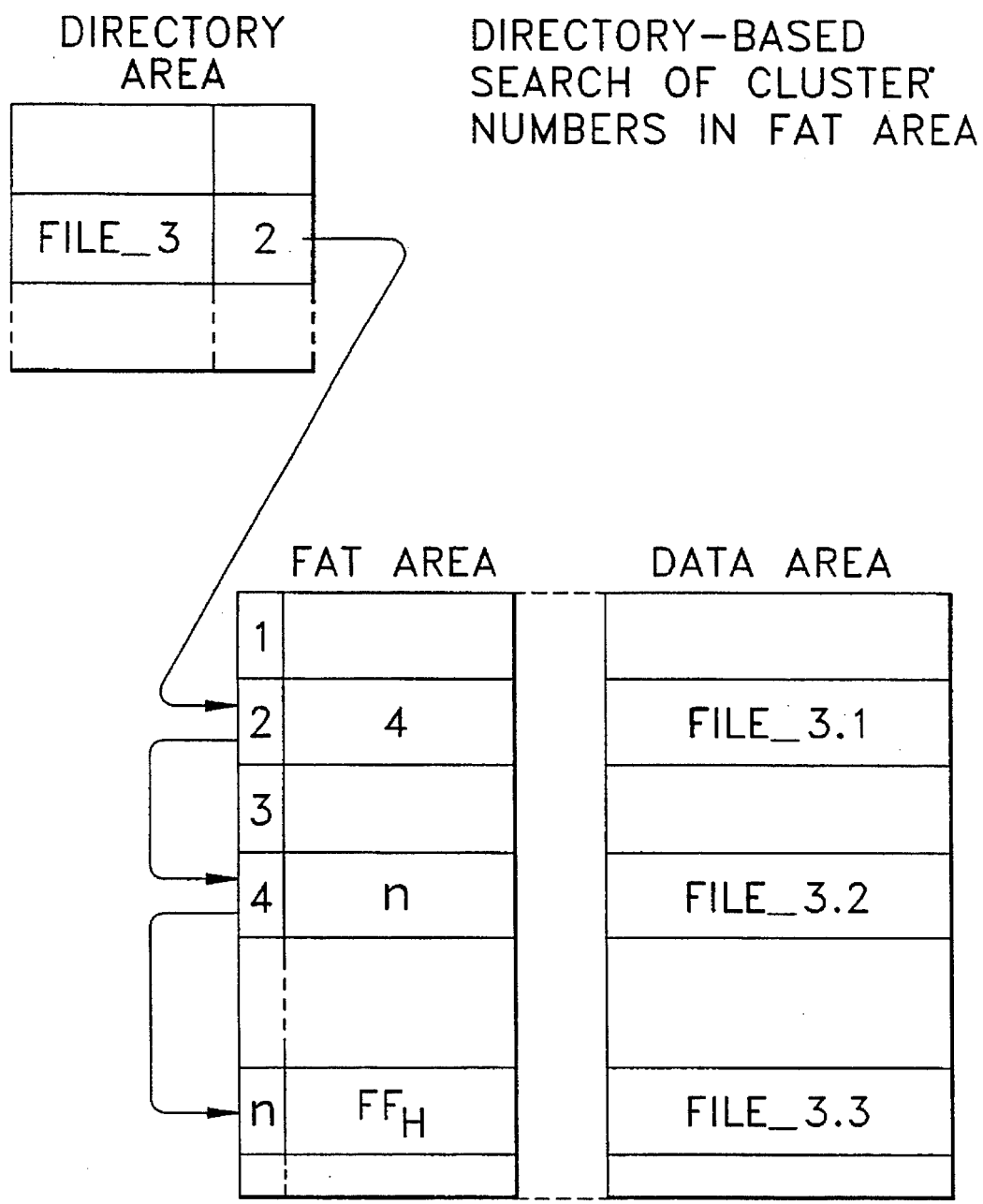
FIG. 7 is an explanatory drawing illustrating a search for cluster numbers in a file allocation table (FAT).

Image file FILE 3 is stored in Format II in the external storage 2. The data are not necessarily stored in contiguous locations but may instead be divided up as shown in FIG. 7. The sequence for reading out FILE 3 from the external storage 2 of the computer system 1 is described with reference to FIG. 7.

To read out FILE 3, the computer system 1 host computer A first accesses the directory area to locate the directory information relating to FILE 3. The data in cluster 2 is obtained from the header cluster number information. Following this, cluster 4 is read out from the cluster 2 area of the FAT. Cluster 4 containing the next portion of the data is then accessed. This read operation is repeated to acquire the data in a continuous flow until the cluster in the FAT area containing an end-of-file marker $FF_H$ is reached.

FIG. 8 illustrates the method of format converting FILE 3 data and directory information read out from the magnetic disk of the external storage 2. Image file data and directory information are stored in the external storage 2, as shown in FIG. 7. The magnetic disk drive 33 reads out image data from the external storage 2 and writes it into the memory of the computer system 1 host computer A.

The format converter program in computer A interprets the attribute information from the first file 73. These attributes which are added would indicate whether the file is an image from a CT scan, MR scan or an X-ray scan. This is added to the directory 75. File name 73 would be indicative of FILE 3 or FILE 4, and directory 75 would be indicative of DIR 3 or DIR 4. The format converter then writes only the data onto the memory of the system computer A. It repeats the similar procedures for the second file, for instance, FILE 4, and writes the DATA 2 onto the immediately adjacent memory which holds the data, DATA 2 from the last file (FILE 3) and so forth. As a result a contiguous block of memory 171 in computer A contains all image data 71. This block 171 of image data 71 is transferred and designated by the format converter program to the optical disk as multiple files or consecutive DATA 1, DATA 2, namely section 271.

At the same time, a 1,024 byte file directory block for instance DIR 3, DIR 4, is generated for each file, for instance, FILE 3, FILE 4. These file directory blocks are written on the optical disk 5 as the optical disk directories. Both the information contained in the file directory blocks and the image data files, for instance, FILE 3, and FILE 4, is the direct result from the format converter program. The format of the file directory block is set out below.

Figure 8A:
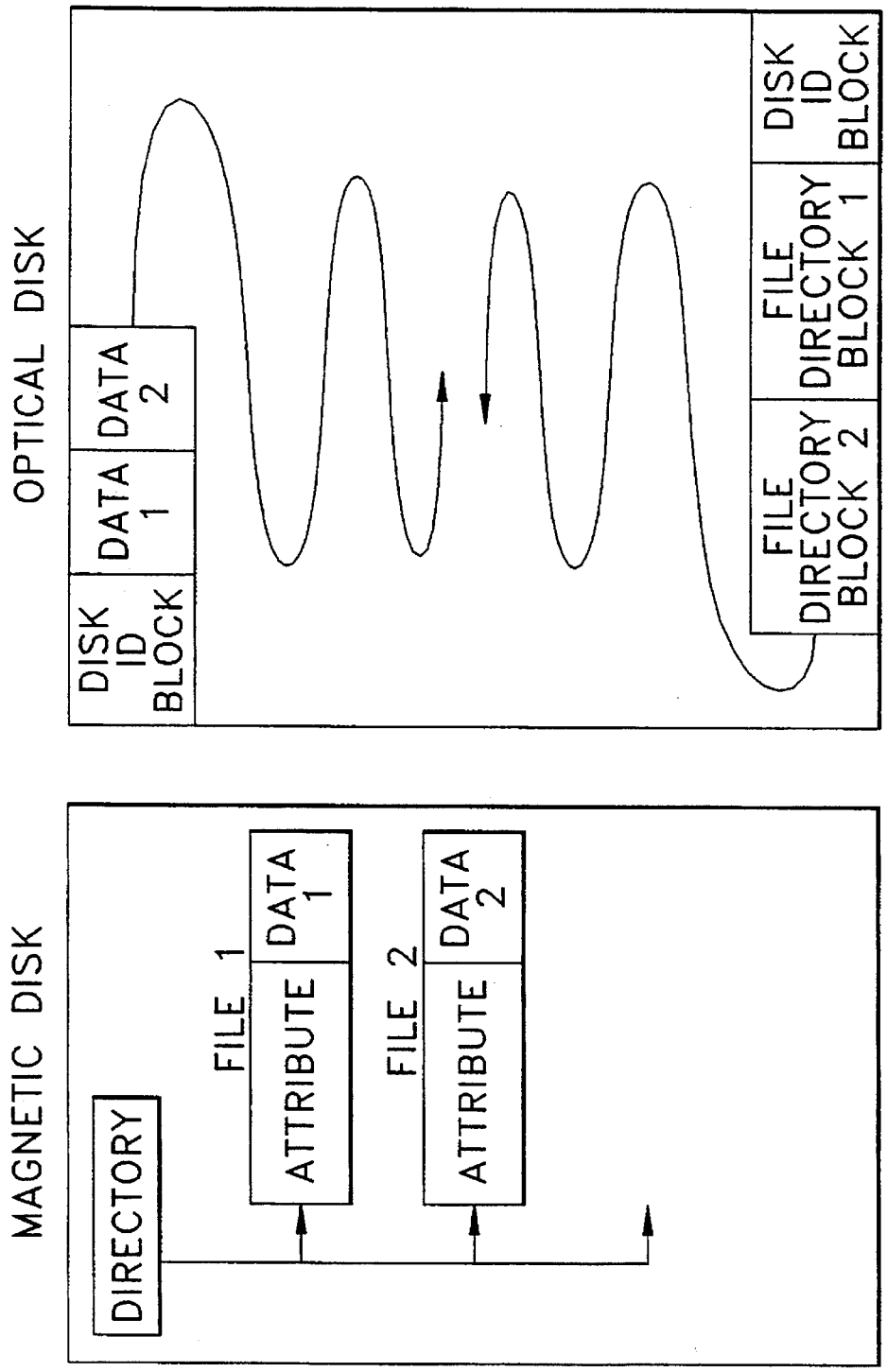

The format converter method of separating the files from the magnetic disk 2 to the optical disk 5 is given in FIG. 8a.

Initially on a magnetic disk 2 the file structure is stored in a non-consecutive fashion with a directory pointing to the proper locations of individual files stored with gaps between them. The format converter transfers this data to the optical disk 5 for storage in a consecutive manner with the files and directories separated and each respectively consecutive. When transferring this data back from the optical disk 5 to the magnetic disk the data is consecutively stored in a manner similar to the optical disk storage. This provides for efficient retrieval of information, such as radiological medical images, from a personal computer storage.

In addition an optical disk 5 ID block is automatically generated when a new optical disk is created.

Disk ID and File Directory Blocks

Disk ID Block:
The disk ID is written at the time of disk initialization. The ID block is written at the very first sector (LBN=0) and also at the very last sector (LBN=MAX). The redundancy is for security.

| | |
|---|---|
| Signature*: | 8 char |
| Version #: | 2 char |
| Protection code: | 16 char (optional password) |
| Disk Name: | 32 char |
| Initialization Date: | 11 char (dd-mmm-yyyy) |
| Comment: | 512 char |

(*Current signature: UCLAPACS version #01)

File Directory Block:
The file directory block is written upon successful archive of a file.

| | |
|---|---|
| File Name*: | 32 char |
| Address: | long int |
| File Size: | long int (specified in bytes) |
| Archival Date: | 11 char (dd-mmm-yyyy) |
| Creation Date*: | 11 char (dd-mmm-yyyy) |
| File Type*: | int (0 = IMAGE, 1 = ASCII, 2 = PICT, etc) |
| Study Type*: | 32 char (for images only) |

(* = user supplied parameters)

FIG. 8 shows the directory information of FIG. 4. This includes information in an operating system dependent format.

To retrieve image data from the optical disk 5, the following steps as illustrated in FIG. 9 are followed:

1. Read all file Directory Blocks 75, for instance, DIR 3, DIR 4, from the optical disk 5.

2. Present all the Directories to the user through computer A.

3. User selects file names, for instance, FILE 3, FILE 4, from the Directories.

4. Each 1,024 byte file directory 75 helps the format converter program to locate the image data 71 from the optical disk 5.

5. The format converter program assigns new proper attribute information and copies the new attributes with the image data 71 onto the magnetic disk 2 and forms a new image file 171.

Image data read out from the external storage 2 and stored in the computer system 1 are in a format in which they can be displayed on the display 3 by means of the display functions of the computer system 1. The format converter 32 retrieves file name 73 from the directory information that has been read into the computer system 1.

Figure 10:
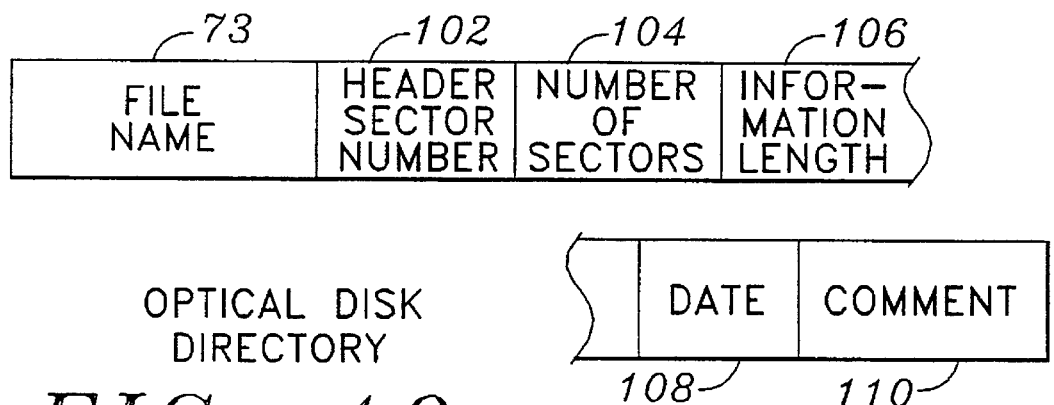
FIG. 10 is an illustration of an optical disk data directory.
Figure 11:
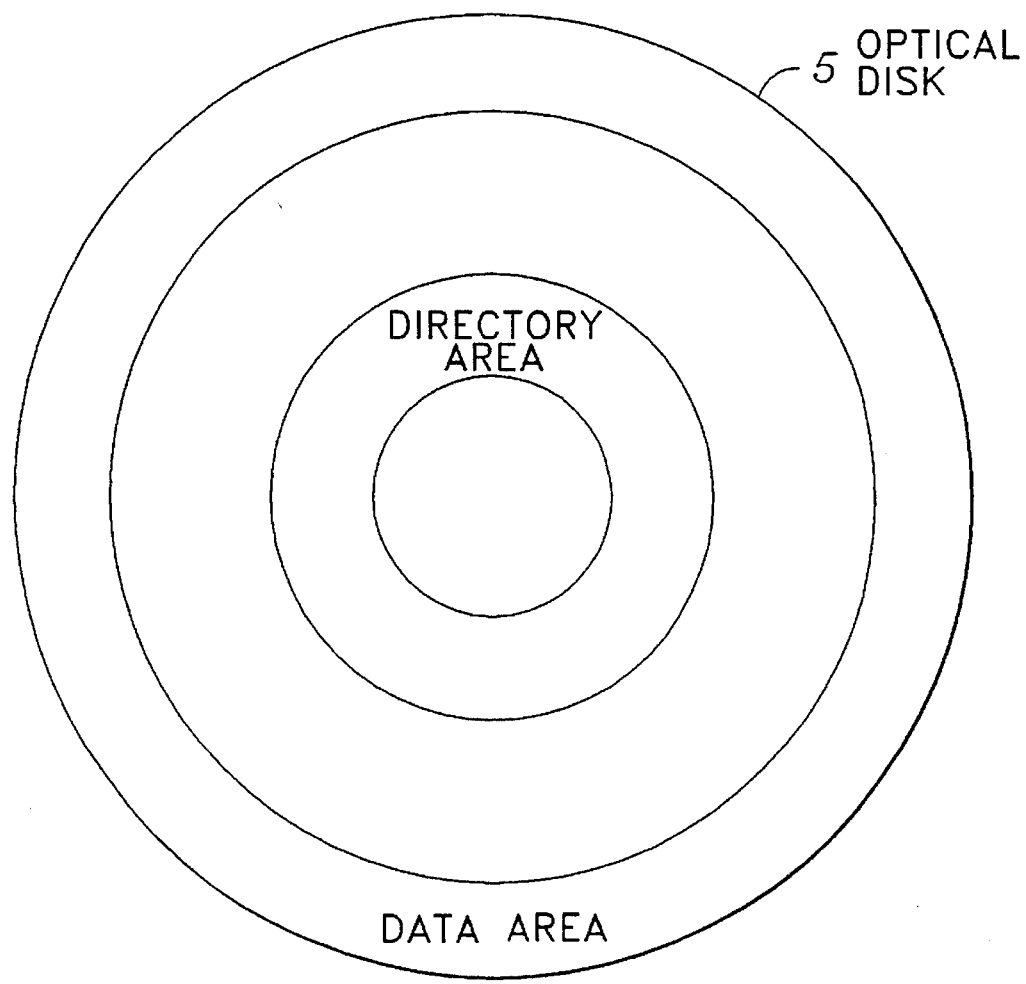
FIGS. 11 and 12 illustrate the data and directory storage areas on an optical disk.

As indicated in FIG. 10, which is the optical disk directory, different items are added to the file name 73. Comment 110 is then added to the header sector number 102, number of sectors 104, information length 106 and date 108 to generate the directory information. This is recorded in the directory area of the optical disk as shown in FIG. 11. Details of this are described below.

The image files are stored on the optical disk 5 as separate data and directory entries. The image data are stored at a location where the images can be recorded as contiguous blocks of data. Directory information is stored at a separate location from the data. Due to this, the format converter 32 shown in FIG. 3 uses the image data length information to calculate the number of sectors required to store the image data on the optical disk 5. Storage areas on the optical disk 5 which are not in use are then located and the header sector numbers of the areas to which image data and directory information can be written are calculated.

Date information is obtained from a real-time clock, for example, provided in the computer system 1. If necessary, a comment can be inputted into the computer system 1 via a keyboard, for example, and will be added to the directory information. The format converter 32 thus generates the directory information stored on the optical disk 5. Image data stored on the optical disk 5 are sequentially read out from the system memory of the computer system 1 and are divided into sector lengths, for example, 1,024 bytes. These form the units in which data on the optical disk 5 are accessed. In this way, an image file that has undergone format conversion is transferred by the optical disk drive 34 into areas designated by the format converter 32.

FIG. 9 illustrates the operation of the image data stored on the optical disk 5 in format I being read out by the computer system 1 and converted to format II by the format converter 32.

As shown in FIG. 11, a data area to store the data and a directory area to store the directory corresponding to the data are established on the optical disk 5. When the image data stored on the optical disk 5 are read out, first the directory information corresponding to the designated file name is read from the directory area of the optical disk 5. The header sector number of the data of the designated file is acquired together with the size, and the data are read out.

Image data read out from the optical disk 5 by the computer system 1 are, as shown in FIG. 9, stored contiguously on the optical disk 5. The format converter 32 extracts the file name from the directory information obtained from the optical disk 5. The conversion date and time, cluster number, size and the required attributes for Format II are added. Directory information for the new Format II is then generated. Following this the image data are written to the external storage 2 by the method shown in FIG. 7.

A format is established that is independent of the storage format, for instance, Format II of the operating system used by the computer system 1. The first and second formats, namely, Format I and Format II, can be converted each way by the format converter 32. In the past, when storage having a different format was used, software was employed to perform a one-to-one conversion. As this merely preserved compatibility among the same specific formats, the range of application was limited.

By providing each computer system 1, 6 and 11 with a format converter 32 written in computer program language of system 1, 6, and 11 respectively, compatibility is maintained over a broader range. In addition, the format converter 32 incorporated by each computer system 1, 6 and 11 is provided with a conversion function for conversion between the operating system-based format of only each respective computer system 1, 6 and 11 and the specific format of the optical disk format 5, 10 and 15. This facilitates the generation process and makes it possible to adapt to the addition of new computer systems 1, 6 and 11.

Figure 12:
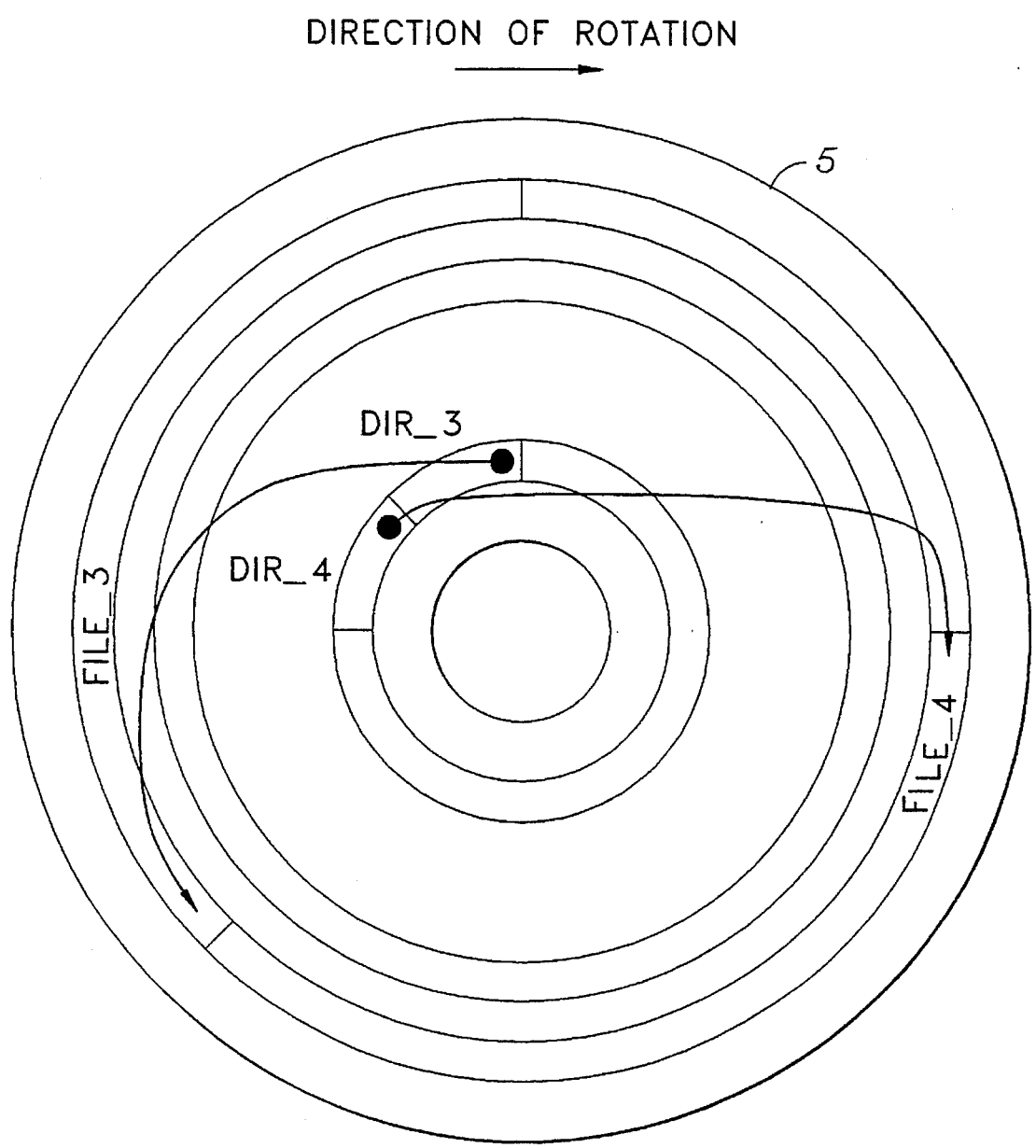

FIG. 12 shows an example of the format in which data are stored on the optical disk 5. The direction of rotation of the optical disk 5 is indicated by the arrow. When the optical disk 5 is inserted into an optical disk drive 4, access starts from a first direction, namely, the innermost part, or track of the disk 5. Data is read out in a continuous stream by moving an optical head of the drive 4 in a straight line toward the outer edge of the disk. The direction of rotation of the disk 5 is fixed and cannot be reversed. Therefore, in order to access the data in a continuous fashion, the data is stored in a continuous, contiguous stream that starts at the inner part of the disk and goes toward the outer edge. The speed of the optical disk drive is usually lower than the speed at which the data are processed, so it has to be performed efficiently.

The file directory information is recorded on the optical disk 5 starting from the inner part of the disk. The substance of the file (data, etc.) is stored in a direction going towards the outer edge or track, namely, a second direction of the disk. The mechanical movements that the optical head needs to make are reduced by storing the substance of the file in contiguous sectors.

The directory has less data than the file and the speed of operation of the disk drive 4 is constant. There is thus a correlation between the directory information contained closer to the center of the disk 5 and occupying less space of the disk 5, and the file data closer to the outer perimeter and occupying more space of the disk. Thus, for the same degree of disk rotation, the appropriate directory and file data is obtained. Also, the spacing on the disk 5 allocated to directory data and file data is efficiently distributed and maximized. By having the directories use space in an outward direction and the file use space in an inward direction, effectively all the space on the disk 5 is used.

In an exemplary fashion assume two files, FILE 3 and FILE 4 are stored on the optical disk. Each file, namely, FILE 3 and FILE 4 consists of directory information and the substance of the file. When the optical disk 5 is inserted into the optical disk drive 4 the computer system 1 reads the directory information of all the files on the optical disk 5 and keeps this information in its internal memory. When a file on the optical disk 5 is accessed, for example, FILE 3 or FILE 4, only the substance of the file is accessed based on the directory information that was read into memory. This enables mechanical movements of the optical disk drive 4 to be reduced. It increases the speed and efficiency of disk access of subsequent files, for instance, from FILE 5 onwards, when large quantities of data have been stored on the optical disk 5.

The directory information includes the file name, header sector number, size, date, and so forth. When data are read from the file, FILE 3, on the optical disk 5, a search is run on the directory information that has already been read in the memory of the computer system 1 to obtain directory information relating to FILE 3. Using the header sector number for read-out and information relating to the size of the file, a command is issued instructing the optical disk drive 4 to read out the data. The data thus read out are written to memory for processing operations, such as conversion, display, and storage on a magnetic disk of the external storage 2. FILE 4 can be accessed using the same procedure.

In the described embodiment each section, namely format conversion, is configured totally or partially in software, firmware or hardware.

The optical disk storage formats are made the same. Thus by employing translation software A, B or C, or circuitry, it is possible to configure an optical disk file system that can be used on any system. Widespread implementation of this translation software A, B or C or circuitry makes it possible for a person to use the same optical disk file system anywhere.

Although this embodiment has been described with reference to optical disks, it is to be understood that the invention is not so limited. The same effect can also be obtained, for instance, by implementing the file system on removable semiconductor files, magnetic disks, digital tape or magnetic cards.

The system of the invention permits for the efficient processing of voluminous data such as radiological medical information on transportable storage media such as small optical disks. The disks can be a write once, read many memory (WORM) disks or disks capable of multiple writings. The disks can be capable of data storage on one or both sides.

In the medical field of application, it is possible with the invented system for a patient to have individual storage of their medical records, and for this to be transported from one computer based processing center to another. In the radiological field, this should minimize the misplacing and loss of images from radiologic examinations and the like which is unfortunately becoming an increasing problem in most hospitals. As the optical disc can be readable irrespective of the operating system of various different computers, the invention markedly extends the ability and accessibility and usefulness of the stored information.

Moreover, although the examples of the invention have been directed to medical type applications, it will be apparent that many other applications exist.

Many other forms of the invention exist each different from the other in matters of detail only. The scope of the invention is to be determined by the following claims.

We claim:

1. A portable optical disk usable among different information processing systems operable on respective specific operating systems respectively different from each other, for transporting information among the different information processing systems,
   (1) wherein each of said different information processing systems comprise:
       (i) an information processor operable on a specific different operating system for processing data and directories;
       (ii) an external storage reactive with the information processor for storing and retrieving therein and therefrom the data and directories in a specific format based on its specific operating system;
       (iii) a format converter reactive with the information processor for converting the data and directories in the specific format to data and directories in said independent format, and vice versa; and
       (iv) an optical disk drive reactive with the information processor and the format converter for storing and retrieving data and directories in the independent format in and from the optical disk, and
   (2) wherein said portable optical disk is formatted in an independent format for storing and reading data and directories therein and therefrom in said independent format which is independent of the formats based on the respective operating systems of the different information processing systems,
   whereby said portable optical disk is compatibly operable with the different information processing systems to transport the data and directories from one to another information processing system through their optical disk drives and format converters irrespective of difference in the operating systems.

2. The disk according to claim 1 wherein the directories are stored sequentially on the optical disk starting from an inner track outwardly and the data are stored sequentially on the optical disk starting from an outer track inwardly.

3. The disk according to claim 2 wherein the data to be stored in the optical disk are divided in accordance with an optical disk sector program.

4. The disk according to claim 1 wherein the data and the directories are each stored, respectively, in a continuous form in one area.

5. The disk according to claim 1 wherein the information data are radiologic medical image data.

6. The optical disk according to claim 3 wherein the information processors are selected from the group of the PC/AT (Trademark), Macintosh (Trademark) and Sun (Trademark) systems.

7. A method of transferring data from a first information processing system to a second information processing system each operable on a specific operating system different from each other,
   (1) wherein each of said first and second information processing systems is provided with
       (i) an information processor operable on its specific operating system for processing data,
       (ii) a magnetic storage disk reactive with the information processor for operatively storing and retrieving data and directories therein and therefrom in a specific format based on the specific operating system of the respective information processing systems, and
       (iii) a format converter reactive with the information processor and magnetic storage disk for converting data and directories in the specific format based on the operating system of the respective information processing systems into data and directories in an independent format which is independent of the formats of the respective specific operating systems, and vice versa,
   (2) wherein there is provided an optical disk in common to the information processors and the format converters of the respective information processing systems for operatively storing and retrieving data and directories therein and therefrom,
   said method comprising:
   (a) combining data usable in the first information processing system with directories in a first specific format based on the first specific operating system of the first information processing system;
   (b) storing the combined data and directories in the first format in areas of the magnetic storage disk in accordance with designation of the first format designated by the format converter of the first information processing system;
   (c) converting the data and directories in the first format into data and directories in the independent format by the format converter of the first information processing system;
   (d) storing the data and directories in the independent format in areas of the optical disk in accordance with designation of the independent format designated by the format converter of the first information processing system;

(e) reading out from the optical disk the data and directories in the independent format by the format converter of the second information processing system; and (f) converting the thus read out data and directories into data and directories in a second specific format based on a second specific operating system of the second information processing system by the format converter of the second information processing system, whereby the data used in the first information processing system become usable in the second information processing system irrespective of the difference in operating systems.

8. The method according to claim 7 wherein the data are stored sequentially in the optical disk in sector length units starting from an outer track inwardly; and the directories are stored sequentially in the optical disk starting from an inner track outwardly.

9. The method according to claim 7 wherein in the first format the data and directories are stored in the magnetic storage disk non-consecutively.

10. The method according to claim 7 wherein the information data are medical data.

11. The method according to claim 7 wherein the first and second information processing systems are selected from the group of the PC/AT (Trademark), Macintosh (Trademark) or Sun (Trademark) systems.

12. A method of processing and transferring data in a first information processing system into a second information processing system, the systems having different operating systems, wherein each of said first and second information processing systems is provided with, respectively, (i) a first or a second information processor for processing data, (ii) a first or a second storage reactive with its associated information processor for storing and retrieving data and directories therein and therefrom, and (iii) a first or a second format converter, wherein there is provided a common storage disk reactive with the respective information processing systems for storing and retrieving data therein and therefrom, said method comprising:

(a) converting data to be transferred to the second information processing system into a first format based on the first specific operating system by the first format converter of the first information processing system so that directories in the first format are generated;

(b) storing and reading the data and directories in the first format in and from the first storage of the first information processing system;

(c) converting the data to be transferred in the first format into an independent format which is independent of the formats of the operating systems of the information processors by the first format converter;

(d) storing the data and directories containing file names in the independent format in the common storage disk through the first format converter;

(e) reading out the data and directories in the independent format from said common storage disk through the second format converter of the second information processing system; and (f) separating the data to be transferred from the directories in the independent format through the second format converter thereby to make the data of the first information processing system utilizable in the second information processing system.

13. The method according to claim 12 wherein the data are stored sequentially in the common storage disk starting from a first location toward a second location and the directories are stored sequentially in the common storage means starting from the second location toward the first location in the independent format.

14. A method of transporting information from a first computer system to a second computer system having respectively different operating systems, wherein the respective computer systems include, respectively, an information processor and a format converter, said method comprising:

(a) causing the first computer system to firstly access a portable optical disk, such that information data and directories therefor which are utilized in the first computer system in a specific format which is based on its operating system are converted into data and directories in an independent format which is specifically designed for the optical disk independently of a format based on the operating systems of the different computer systems and are written in the optical disk through the format converter of the first computer system; and (b) causing the second computer system to secondly access to the optical disk such that the data and directories in the independent format are read out from the optical disk and are converted into data and directories in a specific format which is based on operating system of the second computer system through the format converter of the second computer system, whereby the information data of the first computer system can be read by the second computer system irrespective of difference in the operating systems.

15. The method according to claim 14 wherein the data and the directories are each stored, respectively, in a continuous form in one area of the optical disk.

16. The method according to claim 14 wherein the information data are radiologic medical image data.

17. An information processing system including a plurality of host computers each having its own operating system different from each other for operatingly processing information data and directories in its own specific format based respectively on its own specific operating system, wherein said information processing system includes:

(a) common storage means for operatingly storing therein and reading out therefrom data and directories in an independent format for the common storage means, such format being independent of the formats of the respective host computers, whereby the host computers may be accessed to said common storage means;

(b) a format converter for the host computers for operatingly converting data and directories in a specific format based on its specific operating system into data and directories in the independent format and vice versa;

(c) means for firstly accessing the said common storage means by one of the host computers, whereby data and directories in a specific format based on the operating system of the thus accessed host computer are converted into data and directories in the independent format by the format converter of the accessed host computer, and means for storing the thus converted data and directories in the common storage means; and (d) means for subsequently accessing the common storage means by one of the host computers, whereby data and directories stored in the independent format in said common storage means are read out therefrom and the thus read out data and directories are converted into data and directories in a specific format based on its own specific operating system by the format converter of the thus subsequently accessed host computer, whereby the data an directories of the firstly accessed host computer are utilized in a subsequently accessed host computer irrespective of difference in their operating systems.

18. An information processing system including a plurality of host computers each having its own operating system different from each other for operatingly processing information data and directories in its own specific format based respectively on its own specific operating system, wherein said information processing system includes:

(a) common storage means for operatingly storing therein and reading out therefrom data and directories in an independent format for the common storage means independently of the formats based on operating systems of the respective host computers, whereby any of the host computers may be accessed to said common storage means;

(b) the host computers each including
  (1) a format converter for operatingly converting data and directories in a specific format based on its specific operating system into data and directories in the independent format and vice versa, and
  (2) a first storage means for operatingly storing therein and reading out therefrom data and directories in its specific format based on the operating system of its host computer;

(c) means for firstly accessing the common storage means by any one of the host computers, whereby data and directories in a specific format based on the operating system of the thus accessed host computer are converted into data and directories in the independent format by the format converter of the thus accessed host computer, and means for storing the thus converted data and directories in the common storage means; and (d) means for subsequently accessing the common storage means by one of the host computers, whereby data and directories stored in the independent format in said common storage means are read out therefrom and the thus read out data and directories are converted into data and directories in a specific format for its first storage means of the thus later accessed host computer based on its own specific operating system by the format converter of the thus subsequently host computer, whereby the data and directories of the firstly accessed host computer are utilized in a subsequently accessed host computer irrespective of difference in their operating systems.

19. The system according to either claim 17 or 18, wherein said common storage means includes a portable information storage medium to which the different host computers are accessible.

20. The system according to claim 19 wherein said portable information storage medium comprises an optical disk.

21. A multi system comprising:

(i) different information processing systems each operable respectively on its own operating system, such systems being different from each other; and (ii) common storage means usable in common to said different information processing systems;

wherein each of said different information processing systems includes
  (1) an information processor for utilizing data on its own operating system, and
  (2) a first storage means operative with said information processor for storing therein and reading out therefrom data and directories in a specific format based on its own operation system, said multi system including:

(a) common storage means operatingly storing therein and reading out therefrom data and directories in an independent format for the common storage means independent of any specific formats of the different information processing systems based on the respective operating systems of the different information processing systems;

(b) the different information processing systems each further including a format converter which operatingly converts data utilized in its own information processing system into data and directories in its specific format based on its own operating system for storing the same in its first storage means and also into data and directories in the independent format for storing the same in said common storage means and which also operatingly converts data and directories in its specific format readout from said first storage means and data and directories in the independent format readout from said common storage means into data capable to be utilized by its information processor of its own information processing system;

(c) means for causing any one of the different information processing systems to be accessible to said common storage means, so that data utilized in the thus accessed information processing system are converted into data and directories in the independent format and supplied to said common storage means by the format converter of the thus accessed information processing system, and so that the thus converted data and directories are operatively stored in said common storage means; and (d) means for causing any one of the other different information processing systems to be later accessible to said common storage means, so that the data and directories stored in the independent format in the common storage means are read out, and converted by the format converter of the thus later accessed information processing system into data utilizable in the later accessed information processing system;

whereby different information processing system are enabled to utilize the data utilized in the first accessed information processing system irrespective of a difference in the operating systems.

22. An information processing system comprising:

(i) different computer systems each having their own operating system different from those of the others for operatively processing data and directories on its own specific operating system; and (ii) common storage means provided to said different computer systems for operatingly storing therein and reading out therefrom data and directories;

wherein said information processing system includes:

(a) the common storage means for operatingly storing therein and reading out therefrom data and directories in an independent format for the common storage means independent of the formats based on the operating systems of the different computer systems;

(b) each of said computer systems having
  (1) a host computer for processing information data on its own specific operating system of the computer system,
  (2) a first storage means operable with said host computer on the same operating system as that of the host computer for operatingly storing therein and reading out therefrom data and directories in a specific format based on its own specific operating system, and
  (3) a format converter for converting data and directories in its own specific format based on its own specific operating system into data and directories in the independent format and vice versa;

(c) the common storage means being accessible by the different computer systems so that data and directories in a specific format based on its operating system of the thus accessed one of the computer systems are converted into data and directories in the independent format by its format converter of the thus accessed computer system, and the thus converted data and directories are stored in the common storage means; and (d) said common storage means being accessible by the computer systems other than the first accessed computer systems, so that the data and directories stored in the independent format in said common storage means are read out and converted into data and directories in a specific format based on an operating system of the later accessed computer system by its format converter;

whereby the data of the first accessed computer system are utilized in accessed different computer system irrespective of difference in operating systems.

23. The system according to either claim 21 or 22, wherein said common storage means includes a portable information storage medium to which the different information processing systems are accessible.

24. The system according to claim 23 wherein said portable information storage medium comprises an optical disk.

25. A method of transferring information in a multi information processing system which comprises at least first and second information processing systems
  (1) wherein said first and second information processing systems are operable respectively on a first or a second operating system each different from each other,
  (2) wherein each of said first and second information processing systems includes respectively,
    (i) a first or a second information processor respectively for processing data on its first or second operating system,
    (ii) a first or a second storage respectively reactive with its associated first or second information processor for operatively storing data and directories therein and retrieving data and directories therefrom in a first or a second format based respectively on the first or second operating system of the associated information processor, and
    (iii) a first or a second format converter respectively, and
  (3) wherein there is provided with common storage means to said first and second information processing systems for operatingly storing data and directories therein and retrieving data and directories therefrom, said method comprising the steps of:

(a) forming said first format converter to operatively convert data and directories in the first format based on the first operating system into data and directories in an independent format for the common storage means independently of the first and second formats, and vice versa, (b) forming said second format converter to operatively convert data and directories in the second format based on the second operating system into data and directories in said independent format, and vice versa, (c) causing said first information processing system to access firstly to said common storage means so that data and directories utilized in the first storage of the first information processing system are converted into data and directories in said independent format and the thus converted data and directories are stored in the common storage means through the first format converter of the firstly accessed first information processing system, (d) causing said second information processing system to access secondly to said common storage means so that the data and directories stored in said common storage means in the independent format are read out and converted into data and directories in the second format through the second format converter of the secondly accessed second information processing system, whereby the data utilized in the first information processing system are transferred into the second information processing system irrespective of difference in the operating systems.

26. A method of using common storage means among a multi computer systems comprising respectively at least a first and a second different computer system operable on their respectively own first and second specific operating system, each respectively different from each other, for transferring information from the first to the second computer system, or vice versa,
  (1) wherein each of said first and second computer systems includes a format converter,
  (2) wherein the format converter of the first computer system operatively converts data and directories in a first format based on the first operating system into data and directories in an independent format for common storage means independently of the formats based on any specific operating systems of the respective computer systems, and vice versa, and
  (3) wherein the format converter of the second computer system operatively converts data and directories in a second format based on the second operating system into data and directories in the independent format, and vice versa, said method comprising:

(a) causing said common storage means to be firstly accessed by said first computer system such that data and directories utilized in the first computer system are converted into data and directories in the independent format and the thus converted data and directories are stored in the common storage means through the format converter of the firstly accessed first computer system; and (b) causing said common storage means to be secondly accessed by the second computer system such that the data and directories stored in said common storage means in the independent format are read out and converted into data and directories in the second format through the format converter of the secondly accessed second computer system, whereby the common storage means is commonly used among the multi computer system to thereby transferring data and directories from the first computer system to the second computer system irrespective of difference in the operating systems.

27. A method of using common storage means among multi computer system comprising at least a first and a second different computer system operable respectively on its own first or second specific operating system, each respectively different from each other, for transferring information from the first to the second computer system, or vice versa, (1) wherein each of said first and second computer systems includes a format converter, (2) wherein the format converter of the first computer system operatively converts data and directories in a first format based on the first operating system into data and directories in an independent format for the common storage means independently of any formats based on the specific operating systems of the respective computer systems, and vice versa, and (3) wherein the format converter of the second computer system operatively converts data and directories in a second format based on the second operating system into data and directories in the independent format, and vice versa, said method comprising:

(a) causing said common storage means to be firstly accessed by said first computer system such that data and directories utilized in the first computer system are converted into data and directories in the independent format and the thus converted data and directories are stored in the common storage means through the format converter of the firstly accessed first computer system;

(b) causing said common storage means to be thereafter accessed by said second computer system such that the data and directories stored in said common storage means in the independent format are read out and converted into data and directories in the second format through the format converter of the later accessed second computer system;

(c) causing said common storage means to be secondly accessed by the second computer system such that data and directories utilized in the second computer system are converted into data and directories in the independent format and the thus converted data and directories are stored in the common storage means through the format converter of the secondly accessed second computer system; and (d) causing said common storage means to be thereafter accessed by the first computer system such that the data and directories stored in said common storage means in the independent format are read out and converted into data and directories in the first format through the format converter of the later accessed first computer system;

whereby the common storage means is commonly and interchangeably used among the multi computer system to thereby transfer data and directories from the first computer system to the second computer system, and vice versa, irrespective of difference in the operating systems.

28. The method according to any one of claims 25, 26, or 27 wherein said common storage means is an optical disk in which data are stored sequentially starting from an outer track towards inward direction and the directories are stored sequentially starting from an inner track towards outward direction.

29. A portable optical disk usable in common to first and second information processing systems (1) wherein said first and second information processing systems are operable on a first or a second operating system, each respectively different from each other, and (2) wherein each of said first and second information processing systems includes, respectively, (i) a first or a second information processor respectively operable on its first or second operating system for operatingly processing data, (ii) a first or a second storage respectively reactive with its associated first or second information processor for operatively storing data and directories therein and retrieving data and directories therefrom in a first or a second format based on the first or the second operating system of the associated information processor, and (iii) a first or a second format converter respectively reactive with the first or the second storage and the first or the second information processor for converting data and directories in the first or the second format into data and directories in an independent format for the portable optical disk independently of said first and second formats, and vice versa, said portable optical disk including:

(a) means for causing a first access by said first information processing system so that data and directories utilized in the first storage of the first information processing system are converted into data and directories in said independent format and the thus converted data and directories are stored in the portable optical disk through the first format converter of the firstly accessed first information processing system, and (b) means for causing a second access by said second information processing system so that the data and directories stored in said portable optical disk in the independent format are read out and converted into data and directories in the second format through the second format converter of the secondly accessed second information processing system, whereby the data utilized in the first information processing system are transferred into the second information processing system irrespective of difference in the operating systems.

30. The optical disk according to claim 29, wherein the directories are stored sequentially in the optical disk starting from an inner track outwardly and the data are stored sequentially in the optical disk starting from an outer track inwardly.

31. The optical disk according to claim 29, wherein the data are stored sequentially in the optical disk starting from a first track and the directories are stored sequentially in the optical disk starting form a second track in opposite directions toward each other.

32. A common storage means usable among different information processing systems which are operable on their own specific operating system different from each other, respectively, for transporting information among the different information processing systems, characterized by being formatted in an independent format for storing data and directories therein and retrieving data and directories therefrom.

(1) wherein said independent format is independent of formats based on the respective operating systems of the different information processing systems, and (2) wherein each of said different information processing systems comprise:
   (i) an information processor operable on its specific operating system for processing data and directories;
   (ii) a specific storage provided to react with the information processor for storing and retrieving therein and therefrom the data and directories for its information processor in a specific format based on its specific operating system; and
   (iii) a format converter reactive with the information processor for converting the data and directories in the specific format to data and directories in said independent format and vice versa, and for storing and retrieving data and directories in the independent format in and from the common storage means, whereby said common storage means is compatibly operable with any of the different information processing systems to transport the data and directories from one to another information processing system through their format converters irrespective of difference in the operating systems.

33. The common storage means according to claim 32 which comprises a disk storage medium, wherein the data to be stored in the disk storage medium are divided in accordance with a disk sector program.

34. The common storage means according to claim 32 or 33 which comprises a disk storage medium in which the directories are stored sequentially starting from an inner track outwardly and the data are stored sequentially starting from an outer track inwardly.

35. The common storage means according to claim 33 or 34 wherein the data and the directories are each stored in a continuous form in one area, respectively, of the disk storage medium.

* * * * *

UNITED STATES PATENT AND TRADEMARK OFFICE
CERTIFICATE OF CORRECTION

PATENT NO.   :   5,471,606

DATED        :   November 28, 1995

INVENTOR(S)  :   Huang et al.

Page 1 of 2

It is certified that error appears in the above-identified patent and that said Letters Patent is hereby corrected as shown below:

On title page,
In [75] Inventors: insert --K.-- after the name "Han".
In [73] Assignees: delete "Maxwell" and insert --Maxell--; delete "Ibaraki" and insert --Ibaraki-shi, Osaka--.
In [62] Related U.S. Application Data: delete 541,676 and insert --5,410,676--.
Column 1, line 62: delete "diferent" and insert --different--.
Column 3, line 16: delete "inputted" and insert --input--.
Column 7, line 21: delete "inputted" and insert --input--.
Column 4, line 38: delete "stored" and insert --storage--.
Column 4, line 52: delete "format" and insert --Format--.
Column 4, line 62: delete "used" after the word "particular".
Column 4, lines 66 and 67: delete "FILE 3" and insert --FILE_3--.
Column 5, lines 16, 19, 22, 24, 31, 32, 43, 49, 57 and 60: delete "FILE 3" and insert --FILE_3--.
Column 5, lines 43, 37, 57 and 60: delete "FILE 4" and insert --FILE_4--.
Column 5, lines 44 and 56: delete "DIR 3" and insert --DIR_3--; delete "DIR 4" and insert --DIR_4--.
Column 6, line 53: delete "FILE 3" and insert --FILE_3--; delete "FILE 4" and insert --FILE_4--.
Column 6, line 49: delete "DIR 3" and insert --DIR_3--.
Column 6, line 50: delete "DIR 4" and insert --DIR_4--.
Column 7, lines 33 and 34: delete "format" and insert --Format--.
Column 8, lines 38, 40, 45, 55 and 58: delete "FILE 3" and insert --FILE_3--.
Column 8, lines 39, 40, 45, 46 and 64: delete "FILE 4" and insert --FILE_4--.
Column 8, line 50: delete "FILE 5" and insert --FILE_5--.
Column 13, claim 17, line 6: delete "an" and insert --and--.

UNITED STATES PATENT AND TRADEMARK OFFICE
CERTIFICATE OF CORRECTION

PATENT NO. : 5,471,606
DATED : November 28, 1995
INVENTOR(S) : Huang et al.

It is certified that error appears in the above-indentified patent and that said Letters Patent is hereby corrected as shown below:

Column 18, claim 31, line 62, delete "form" and insert --from--.

Signed and Sealed this

Twenty-third Day of April, 1996

Attest:

BRUCE LEHMAN

Attesting Officer    Commissioner of Patents and Trademarks